United States Patent [19]

Shigematsu et al.

[11] 4,229,4

[45] Oct. 21, 1

[54] METHOD FOR CONTROLLING VIRAL DISEASES IN PLANTS

[75] Inventors: Taichiro Shigematsu, Machida; Tetsuya Shibahara, Yamato; Tetsuo Nakajima, Kawasaki, all of Japan

[73] Assignee: Mitsubishi Chemical Industries Limited, Tokyo, Japan

[21] Appl. No.: 40,077

[22] Filed: May 17, 1979

[30] Foreign Application Priority Data

May 30, 1978 [JP] Japan .................................. 53-64743
Feb. 20, 1979 [JP] Japan .................................. 54-18794

[51] Int. Cl.[3] ...................... A01N 43/84; A01N 43/86; A01N 43/40; A01N 43/36

[52] U.S. Cl. .................................... 424/78; 424/248.4; 424/267; 424/274

[58] Field of Search ....................... 424/78, 267, 248.4, 424/274; 260/567.6 P; 526/204

[56] References Cited

U.S. PATENT DOCUMENTS

| | | | |
|---|---|---|---|
| 3,288,770 | 11/1966 | Butler | 526, |
| 4,053,512 | 10/1977 | Panzer et al. | 260/567 |
| 4,113,709 | 9/1978 | Quinlan | 42 |
| 4,151,202 | 4/1979 | Hunter et al. | 260/567 |

FOREIGN PATENT DOCUMENTS

| | | | |
|---|---|---|---|
| 2750777 | 5/1978 | Fed. Rep. of Germany | 42 |
| 45-1457 | 1/1970 | Japan . | |

*Primary Examiner*—Douglas W. Robinson
*Attorney, Agent, or Firm*—Bierman & Bierman

[57] ABSTRACT

Chemicals containing an effective amount of a poly of a specified salt of diallylamine derivative and/ diallyl quarternary ammonium salt exhibit a remark effect of preventing agricultural plants from being fected with viral diseases in plants. A method for trolling viral diseases in plants by using an effec amount of such polymer is described.

17 Claims, No Drawings

METHOD FOR CONTROLLING VIRAL DISEASES IN PLANTS

BACKGROUND OF THE INVENTION

1. Field of the Invention

This invention relates to a method for controlling viral diseases in plant by using the chemicals containing an effective amount of a specified polymer as an active ingredient.

2. Description of the Prior Art

It is known that the plants such as tobacco, tomato, Spanish paprika, potato, cowpea, French bean, cucumber, water melon, strawberry, melon, Chinese cabbage, radish and the like, which are cultivated in various manners of culture such as field culture, glasshouse culture, etc., tend to suffer from mosaic diseases and dwarfing diseases to plant viruses such as a tobacco mosaic virus (hereinlater abbreviated as TMV), cucumber mosaic virus (hereinlater abbreviated as CMV), cucumber green mottle mosaic virus (hereinlater abbreviated as CGMMV), potato virus X (hereinlater abbreviated as PVX), lettuce mosaic virus (hereinlater abbreviated as LMV), melon necrotic spot virus (hereinlater abbreviated as MNSV) and the like, thus frequently incurring a great deal of damage to these plants. Since these plant viruses generally exist in various plants, weeds, seeds, soils, roots remaining in soil, the plant suffers readily contagion to the viruses by the suction of plant juice by the insects, by artificial contact (such as with farm appliances, hand, or clothes), or by the contact with the virus-containing soil during transplantation or planting, etc. If a primary contagion takes place, there is a danger that the plant virus spreads throughout the field or other culture systems by the artificial contact such as the farming work.

Various chemicals for controlling such plant virus diseases are known including: antibiotics and base in nucleic acid-like substances both of which have a function of suppressing multiplication of plant viruses; and the juices of plants such as dyer's grape (*Phytaracca decandra*), goosefoot, carnation, etc., and polymeric materials derived from living body such as casein, alginic acid, etc, both of which have a function of preventing contagion of plant viruses to the plants. However, most of the former substances exhibit toxicity against man and domestic animals as well as plants and thus have never been used in practical application. The latter substances are of natural origin and thus a difficulty is encountered in mass-producing the substances having uniform composition. Only one instance which has been practically used is a chemical containing sodium alginate as a principal component (wettable powder of alginic acid: Registration No. 13440 at the Minister of the Agriculture and Forestry, Japan).

Therefore, if a plant has been once infected with a disease in the culture field, the secondary contagion is generally prevented by a passive manner that the infected plants are removed and burned as soon as they are found.

We made the intensive examination to develop the chemicals for controlling viral disease in plants which are innoxious and high in efficacy. As the result, we found the polymerization products of the specified salts of diallylamine derivatives and diallyl quaternary ammonium salts have high activity of controlling viral diseases in plant, and completed the present invention.

It is known that some of these polymers are usec flocculants or antistastic agents (U.S. Pat. 3,288,770), but not that they have high activity of c trolling viral diseases in plants.

SUMMARY OF THE INVENTION

Thus, an object of the present invention is to pro a method for controlling viral diseases in plants by u an effective amount of the specified polymer whic innoxious and high in control efficacy. According to present invention, the object is attained.

This invention relates to a method for control viral diseases in plants by applying an effective amc of a polymer obtained by polymerizing one or compounds expressed by the following formula (I).

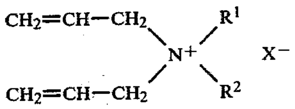

wherein, $R^1$ and $R^2$ represent a hydrogen atom o alkyl group having 1 to 5 carbon atoms which ma substituted by a halogen atom, a hydroxyl group cyano group. $R^1$ and $R^2$ may be the same or not, they may form a heterocyclic ring with the nitro they attach to. X represent a halogen atom.

DETAILED DESCRIPTION OF THE INVENTION

The present invention relates to a method for con ling viral diseases in plants by using an effective am of a polymer obtained by polymerizing one or two k of compound expressed by the above formula (I).

In the formula (I), $R^1$ and $R^2$ may represent the s or not, and are a hydrogen, alkyl group having carbon atoms which may be substituted by a hal atom, a hydroxyl group or a cyano group. $R^1$ an may form a heterocyclic ring with a nitrogen the tach to.

The alkyl group to be used is that having 1 to 5 bon atoms, preferably not more than 3, concrete methyl group, an ethyl group, a n-propyl group.

The substituted alkyl group is that having 1 to 3 bon atoms, concretely a β-hydroxyethyl group, cyanoethyl group, a β-hydroxy-γ-halopropyl grou $R^1$ and $R^2$ may form a heterocyclic ring with nitrogen they attach to, concretely a pyrrolidine ri piperidine ring or a morphorine ring.

X represents a halogen atom such as a chlorine a bromine atom and an iodine atom, or an acid ra such as $HSO_4^-$, $HSO_3^-$, $HCOO^-$ and $CH_3CO$ preferably a halogen atom.

The concrete examples of the compound expr by the above formula (I) are divided into two grou follows.

(A) Salts of the following diallylamines:

diallylamine,
diallylmethylamine,
diallylethylamine,
diallyl-n-propylamine,
diallyl-iso-propylamine,
diallyl-β-hydroxyethylamine,
diallyl-β-cyanoethylamine and
diallyl-β-hydroxy-γ-chloropropylamine.

Among the above salts, hydrohalides are prefe hydrochloride is more preferable.

) Quaternary ammonium salts of diallylamines:
/l dimethyl ammonium salt,
/l diethyl ammonium salt,
/l di-n-propyl ammonium salt,
/l methyl-β-hydroxyethyl ammonium salt,
/l ethyl-β-hydroxyethyl ammonium salt,
/l methyl ethyl ammonium salt,
/l methyl-β-cyanoethyl ammonium salt,
/l ethyl-β-cyanoethyl ammonium salt,
/l methyl-n-propyl ammonium salt,
/l methyl-β-hydroxy-γ-chloropropyl ammonium t,
/l pyrrolidinium salt,
/l piperidinium salt and
/l morpholinium salt.

nong the above ammonium salts, ammonium ha- are preferable. Ammonium chloride and ammo- bromide are more preferable.

the copolymer in the present invention, the poly- zation product of a hydrohalide of diallylamine in ıbove (A) group and a diallyl quaternary ammo- halide in the above (B) group is preferable, con- ly a copolymer of (3-chloro-2-hydroxy)propyl /lamine hydrochloride and dimethyl diallyl ammo- chloride.

ıe polymers are prepared by a known method. For nce, the raw material monomer compound ex- ed by the formula (I) which is solved in a solvent as water, methanol, ethanol, dimethylsulfoxide, thyl acetamide and dimethyl formamide is polimer- at the temperature of 0°-80° C. in the presence of oolymerization catalyst, for example, ammonium ılfate, potassium persulfate, aa'-azobisisobutyroni- tert-butyl hydroperoxide, di-tert-butyl peroxide, ne hydroperoxide. (Japanese Pub. No. 1457/1970) preparing a copolymer, the molar ratio of (A) a ohalide of diallylamine derivative and (B) a diallyl ernary ammonium halide is not limited, but (B)=0.05-10, especially 0.5-7 is preferable.

is presumed that the structure of the prepared poly- has the following unit at least in a part as a compo-

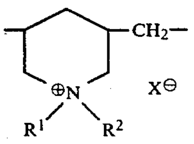

ein $R^1$, $R^2$ and X have the same meanings as de- in the foregoing formura (I).

ıe rotational viscosity of the polymer used in the nt method is not limited specifically, but deter- d by considering the easiness in application of the ıical and its antiviral activity. Usually, the rota- l viscosity of 0.2 wt % aqueous solution of homo- mer is in the range of 2.0-30 cps, preferably 3.0-20 at 20° C., and that of copolymer is in the range of 0 cps, preferably 2.0-20 cps. The polymer used in resent method is water soluble.

ıe polymer described above may be used, as it is, as control agent but is generally admixed with adju- to use in the form of a wettable powder, a dust, an sion or a solution.

the case of the dust, a carrier and a surface active t are employed to mix with the polymer. Suitable ıples of the carrier include kaolin, bentonite, talc, clay, white carbon and diatomaceous earth. These carriers may be used singly or in combination.

When using in the form of a wettable powder, the surface active agents are employed so as to improve the dispersiveness of the chemical in water and to increase the extend effect when sprayed on plants. (In this specification, the wettable powder means that which does not contain the carriers.) A wide variety of surface active agents including nonionic active agents and cationic active agents are usable for this purpose. Suitable agents include nonionic active agent; such as polyoxyethylene alkylallyl ether, polyoxyethylene sorbitan monolaurate, etc. These agents may be used singly or in combination, which depends on the purpose in end use of the wettable powder.

Further, when the chemical is used as an emulsion or a solution, water and/or a solvent miscible with water is employed aside from the above-mentioned two types of adjuvants. Such solvents include alcohols such as methyl alcohol, ethyl alcohol and ethylene glycol, ketones such as acetone, ether such as dioxane and tetrahydrofuran, amides such as dimethylformamide, and a mixture thereof.

When the polymer is applied as the control agent in the form of a wettable powder, 70-99 parts by weight of the polymer and 1-30 parts by weight of a surface active agent are mixed in a suitable ratio. In application, the mixture is diluted with water to have a desired concentration and applied for the control.

To apply the polymer in the form of an emulsion or a solution, 10-60 parts by weight of the polymer, 20-90 parts by weight of a solvent and 1-20 parts by weight of a surface active agent are mixed in desired ratios. Then, the mixture is applied by dilution with water similarly to the case of the wettable powder.

In the case of the dust, 1-20 parts by weight of the polymer, 80-98 parts by weight of a carrier and 1-5 parts by weight of a surface active agent are uniformly mixed in desired ratios and applied.

The chemical for the plant virus disease control according to the invention can effectively control an contagion of viruses such as TMV, CMV, CGMMV, etc., by soil treatment or by spraying on stems and leaves of growing plants. With the case of the wettable powder, emulsion or solution, a solution having a concentration of the effective component ranging 500-5000 ppm is sprayed on plants or irrigated into soils in an amount of 50-3000 l per 10 ares. With the dust, it is admixed with soils in an amount of 300-10000 g/10 ares as effective component.

As a matter of course, the polymer may be used by mixing with other active components which do not impede the antiviral activity of the polymer, e.g., fungicide, insecticide, miticide, etc.

The chemicals of this invention is used by the method of the soil treatment or the foliar spray, generally the foliar spray. These methods may be used together.

The chemicals of this invention are effective to the mosaic diseases by the following viruses, TMV, CMV, CGMMV, PVX, LMV, MNSV and the like, especially, TMV, CMV and CGMMV.

The chemicals of this invention are effective to prevent the viral diseases from spreading over the plants belong to Solanaceae, Cucurbitaceae, Luguminosae, Rosaceae and Cruciferae, concretely, tobacco, tomato, Spanish paprika, potato, cucumber, melon, watermelon, cowpea, French bean, radish, Chinese cabbage, strawberry and the like, especially, Solanaceae such as tobacco, tomato and Spanish paprika, and Cucurbitaceae such as cucumber, watermelon and melon.

The present invention will be particularly described by way of the following examples showing preparations of polymers and experiments of the chemicals using such polymers as effective component. These examples are for purposes of exemplification only and in no way are intended to limit the scope of the invention.

Preparative Example 1:

10.5 g of dimethyl diallyl ammonium chloride and 19.5 g of dimethyl sulfoxide were introduced into a test tube, to which 210 mg of ammonium persulfate was added as a polymerization catalyst, and, after deairing, nitrogen gas was charged into the reaction system. The test tube was sealed to submit to the polymerization reaction in a bath at a constant temperature of 50° C. for 48 hours. After polymerization, the tube was unsealed and a small amount of methanol was added to the solidified polymerization product to produce viscous solution, which was poured into a large amount of acetone to precipitate a gell, followed by filtrating, washing with acetone and drying the gell under a reduced pressure thereby obtaining 6.8 g of aimed polymer (No. 1).

The above process was repeated using various compounds to obtain polymers (Nos. 3, 4, 5, 6, 11, 12 and 13). The presumed structural formulae and rotational viscosities (cps) of these polymers are indicated in Table 1. In the present specification, the rotational viscosity was obtained by measuring 0.2 wt % aqueous solution of polymer by a rotational viscometer of Shibaura System Co., Vismetron VSA-L. In Table 1, n represents a natural number of polymerization degree.

Preparative Example 2

20 g of diallyl methyl-β-hydroxyethyl ammonium chloride and 20 g of water were introduced into a test tube, to which 0.8 g of cumene hydroperoxide was added as a polymerization catalyst, and, after deairing, nitrogen gas was charged into the reaction system. The test tube was sealed to submit to the polymerization reaction in a bath at a constant temperature of 50° C. for 48 hours. After polymerization, the tube was unsealed and the produced viscous solution was added to a large amount of acetone to precipitate a gell, followed by filtrating, washing with acetone and drying the gell under a reduced pressure thereby obtaining 14.8 g of aimed polymer (No. 8).

The above process was repeated using various compounds to obtain polymers (Nos. 7, 9 and 10).

The structural formulae and rotational viscosities (cps) are indicated in Table 1.

Preparative Example 3

The procedure of Preparative Example 1 was repeated except that the polymerization temperature was 30° C. thereby obtaining aimed polymer (No. 2).

Preparative Example 4

9 g of dimethyl diallyl ammonium chloride, 1 g of (3-chloro-2-hydroxy)propyl diallylamine hydrochloride and 10 g of dimethyl sulfoxide were introduced into a test tube, to which 210 mg of ammonium persulfate was added as a polymerization catalyst, and, after deairing, nitrogen gas was charged into the reaction system. The test tube was sealed to submit to the polymerization reaction, in a bath at a constant temperature of 50° C. for 24 hours. After polymerization, the tube was u sealed and a small amount of methanol was added to t solidified polymerization product to produce visco solution, which was added to a large amount of aceto to precipitate a gell, followed by filtrating, washi with acetone and drying the gell under a reduced pr sure thereby obtaining 6.9 g of aimed polymer (No. 1 The structural formula and rotational viscosity (cps) polymer No. 14 are indicated in Table 1.

Preparative Example 5

7.5 g of dimethyl diallyl ammonium chloride, 1.25 of (3-chloro-2-hydroxy) propyl diallylamine hydrochl ride and 3.75 g of water were introduced into a t tube, to which 180 mg of ammonium persulfate as polymerization catalyst, and, after deairing, nitrog gas was charged into the reaction system. The test tu was sealed and to submit to the polymerization reacti in a bath at a constant temperature of 45° C. for hours. Thus produced viscous solution was added tc large amount of acetone to precipitate a white ge followed by filtrating and drying the gell under a duced pressure at 45° C. thereby obtaining 5.5 g polymer (No. 15).

The structural formula and rotational viscosity of tl polymer is indicated in Table 1.

The polymer showed an intrinsic viscosity of 0.407 0.1 N NaCl aqueous solution at 25° C.

Preparative Example 6

The procedure of Preparative Example 5 was peated except that the polymerization temperature w 60° C. thereby obtaining aimed polymer (No. 16).

The polymer showed an intrinsic viscosity of 0.375 0.1 N NaCl aqueous solution at 25° C.

Preparative Example 7

The procedure of Preparative Example 5 was peated except that the amounts of water and ammoni persulfate were 5.25 g and 210 mg respectively and tl the polymerization temperature was 60° C. there obtaining aimed polymer (No. 17).

The polymer was indicated in Table 1.

The polymer showed an intrinsic viscosity of 0.175 0.1 N NaCl aqueous solution at 25° C.

Preparative Example 8

The procedure of Preparative Example 5 was peated except that the used amounts of dimethyl dial ammonium chloride and (3-chloro-2-hydroxy) pro diallylamine hydrochloride were 6.4 g and 1.6 g resp tively thereby obtaining aimed polymer (No. 18).

The procedure of Preparative Example 5 was peated except that the used amounts of dimethyl dial ammonium chloride, (3-chloro-2-hydroxy) propyl di lylamine hydrochloride and water were varied as f lows thereby obtaining aimed polymers.

| dimethyl diallyl ammonium chloride (g) | (3-chloro-2-hydroxy) propyl diallylamine hydrochloride (g) | water (g) | polym No. |
|---|---|---|---|
| 5 | 5 | 4.3 | 19 |
| 3 | 7 | 4.2 | 20 |
| 1 | 9 | 4.3 | 21 |

These polymers are indicated in Table 1.

TABLE 1
| lymer No. | Pressumed Structural Formula | Rotational Viscosity (cps) |
|---|---|---|
| 1 | 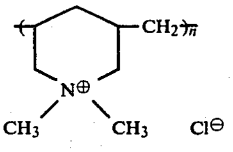 | 4.4 |
| 2 | 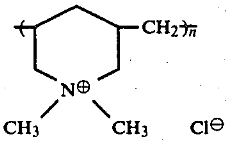 | 5.2 |
| 3 | 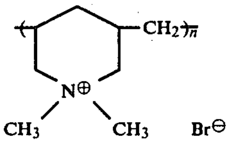 | 3.1 |
| 4 | 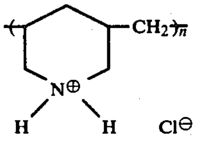 | 3.7 |
| 5 | 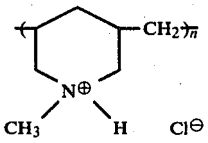 | 4.2 |
| 6 | 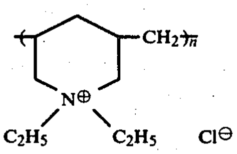 | 4.9 |
| 7 | 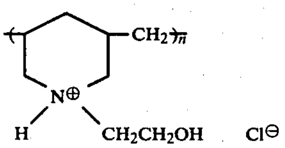 | 4.6 |
| 8 | 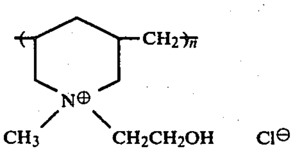 | 4.8 |
| 9 | 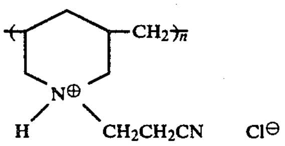 | 4.3 |
| 10 | 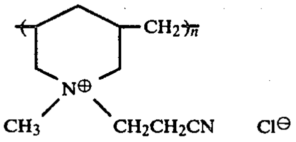 | 4.9 |

TABLE 1-continued
| Polymer No. | Pressumed Structural Formula | Rotational Viscosity (cps) |
|---|---|---|
| 11 | 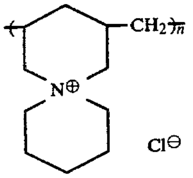 | 4.7 |
| 12 | 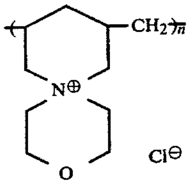 | 3.8 |
| 13 | 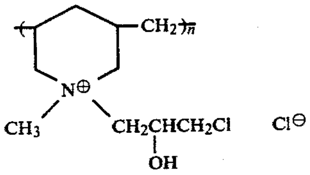 | 4.2 |
| 14 | 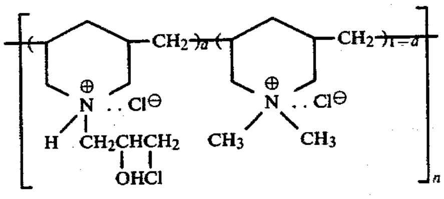 | 5.65 |
| 15 | 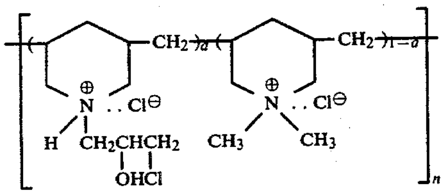 | 4.72 |
| 16 | 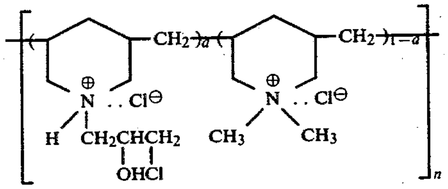 | 4.23 |
| 17 | 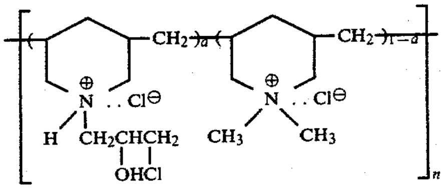 | 2.16 |
| 18 | 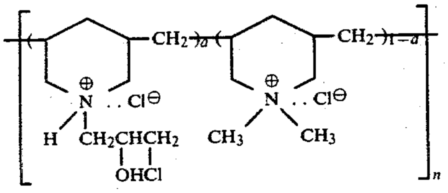 | 3.16 |

TABLE 1-continued

| lymer No. | Pressumed Structural Formula | Rotational Viscosity (cps) |
|---|---|---|
| !9 | 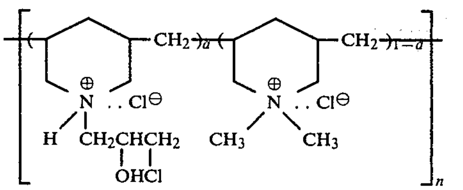 | 2.63 |
| !0 | 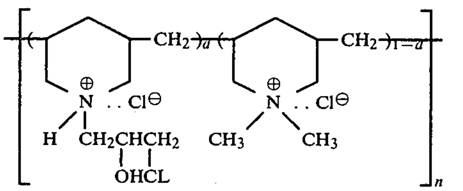 | 2.87 |
| !1 | 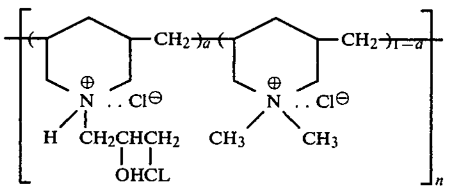 | 2.14 |

EXAMPLE 1

ꓥqueous solutions containing 2000 ppm and 1000 m of each of the polymers (Nos. 1-21) indicated in ble 1 were, respectively, sprayed over potted to- ꞇco seedlings (Xanthi nc) of leaf stages of 10-11 in an ount of 50 ml per seedling by means of a spray gun. ter drying in air, each seedling was inoculated with a rified TMV solution ($5\times10^{-7}$ g/ml) by an ordinary borundum method and then allowed to stand in a sshouse for 3-4 days thereby causing local lesions to m on leaves.

Гhe number of the formed local lesions was checked comparison with that obtained with non-treated dlings to determine a inhibition rate of TMV local ion formation for each test solution.

Гhe purified TMV solution was prepared by isolating ɅV from a sap of TMV-infected leaves and purifying y means of an ultra-centrifuge.

Гhe test results are shown in Table 2.

Furthermore, chemical damage was observed by aying 2000 ppm of each of the polymers (Nos. 1-21) er tobacco seedlings (Bright Yellow) of leaf stages of -11, with the result that neither withering of the seed- g nor chemical spot was observed.

TABLE 2

| Polymer No. | Inhibition rate of TMV local lesion formation (%) 2000 ppm | 1000 ppm |
|---|---|---|
| 1 | 93.6 | 87.3 |
| 2 | 95.1 | 87.5 |
| 3 | 89.7 | 82.7 |
| 4 | 92.4 | 85.3 |
| 5 | 92.7 | 84.1 |
| 6 | 93.0 | 86.2 |
| 7 | 90.2 | 84.3 |
| 8 | 95.7 | 88.5 |
| 9 | 91.5 | 83.7 |
| 10 | 92.5 | 84.6 |
| 11 | 88.2 | 80.4 |
| 12 | 90.7 | 82.6 |

TABLE 2-continued

| Polymer No. | Inhibition rate of TMV local lesion formation (%) 2000 ppm | 1000 ppm |
|---|---|---|
| 13 | 93.8 | 85.2 |
| 14 | 93.4 | 87.6 |
| 15 | 98.9 | 91.4 |
| 16 | 93.4 | 87.6 |
| 17 | 88.5 | 82.5 |
| 18 | 90.1 | 81.8 |
| 19 | 90.3 | 77.5 |
| 20 | 94.5 | 84.6 |
| 21 | 93.7 | 84.2 |
| non-treated | 0 | 0 |

Inhibition rate of TMV local lesion formation =

$$\left(1 - \frac{\text{Number of Lesions in Treated Seedling}}{\text{Number of Lesions in Non-treated Seedling}}\right) \times 100\ (\%)$$

EXAMPLE 2

Aqueous solutions of each of the polymers indicated in Table 3 with concentrations of 2000 ppm and 1000 ppm were each sprayed over young cowpea plants growing for 10 days after seedling (*Vigna sinenis var, sesguipendalis,* cv *Kurodane sanjaku*) in an amount of 5 ml per plant by means of a spray gun. After drying in air, a purified CMV inoculation solution (with a concentration of $10\times10^{-6}$ g/ml) was inoculated into the plants by an ordinary carborundum method, followed by allowing to stand in a greenhouse for 3-4 days to cause local lesion to form on leaves of the plant. The number of the formed local lesions was checked and compared with that obtained with the non-treated plant to determine a inhibition rate of CMV local lesion formation for each test solution. The test results are shown in Table 3 below.

TABLE 3

| Polymer No. | Inhibition rate of CMV local lesion formation (%) 2000 ppm | 1000 ppm |
|---|---|---|
| 1 | 94.2 | 86.6 |
| 4 | 93.5 | 85.4 |
| 5 | 91.9 | 80.8 |
| 6 | 93.8 | 87.1 |
| 8 | 95.4 | 89.7 |
| 10 | 91.7 | 82.6 |
| 13 | 93.5 | 87.2 |
| 15 | 95.2 | 89.6 |
| 16 | 91.8 | 83.2 |
| 18 | 90.5 | 84.5 |
| 20 | 93.1 | 82.1 |
| 21 | 93.5 | 87.2 |
| Non-treated | 0 | 0 |

Inhibition rate of CMV local lesion formation =

$$\left(1 - \frac{\text{Number of Lesions in Treated Plant}}{\text{Number of Lesions in Non-treated Plant}}\right) \times 100\ (\%)$$

EXAMPLE 3

Tobacco seedlings of Bright Yellow to be a kind of systemic infection plant were used to examine the effect of the chemicals of the invention in a field artificially contaminated with TMV*.

Note: *A planting hole in the field in which the seedling was planted was charged with a soil which had been mixed with dry powder of tobacco leaves attacked with TMV in an amount of 0.5 g per l of the soil.

Aqueous solution having a concentration of 2000 ppm of the polymers Nos. 1, 5, 6, 8, 14, 15, 16 and 21 indicated in Table 1 were each sprayed over the tobacco seedlings by means of a sprayer of a knapsack type in an amount of 50 ml per seedling. After drying in air, the sprayed seedlings were planted in the contaminated field.

About one month after the planting, the seedlings were observed to check how many seedlings were infected with the mosaic disease.

The test results are shown in Table 4 below.

TABLE 4

| Polymer No. | Infected Seedlings/ Total of Seedlings | Preventive Value (%) |
|---|---|---|
| 1 | 2/15 | 87 |
| 5 | 4/15 | 73 |
| 6 | 3/15 | 80 |
| 8 | 3/15 | 80 |
| 14 | 4/16 | 75 |
| 15 | 2/16 | 88 |
| 16 | 2/16 | 88 |
| 21 | 3/16 | 81 |
| Non-treated | 15/15 | 0 |

Preventive Value =

$$\left(1 - \frac{\text{Number of Infected Seedlings in treated case}}{\text{Number of Infected Seedlings in non-treated case}}\right) \times 100\ (\%)$$

EXAMPLE 4

Tomato seedlings (kind: Yuyake) were used to examine the effect of the chemicals of the invention in a field artificially contaminated with TMV.

An aqueous solution containing 2000 ppm of each of the polymers corresponding to Nos. 1, 5, 8, 14, 15 and 21 indicated in Table 1 was applied to the seedlings, prior to planting, in an amount of 50 ml per seedling and also to the planting hole in an amount of 500 ml by means of a sprayer of a knapsack type. After drying the seedlings in air, the seedlings were each planted in the hole. About one month after the planting, the seedlings which were infected with the mosaic disease we checked. The test results are shown in Table 5.

Note: The hole was charged with a soil which w mixed with a dry powder of tomato leaves attack with TMV in an amount of 0.5 g per l of the soil.

TABLE 5

| Polymer No. | Infected Seedlings/ Total of Seedlings | Preventive Value (%) |
|---|---|---|
| 1 | 2/20 | 90 |
| 5 | 4/20 | 80 |
| 8 | 4/20 | 80 |
| 14 | 2/20 | 90 |
| 15 | 2/20 | 90 |
| 21 | 4/20 | 80 |
| Non-treated | 20/20 | 0 |

Preventive Value =

$$\left(1 - \frac{\text{Number of Infected Seedlings in treated case}}{\text{Number of Infected Seedlings in non-treated case}}\right) \times 100\ (\%)$$

We claim:

1. A method for preventing viral diseases in plar comprising applying to said plants an antiviral effecti amount of a polymer produced by the polymerization one or two compounds expressed by the following ge eral formula:

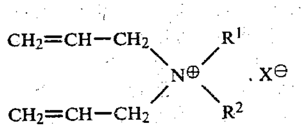

wherein $R^1$ and $R^2$, which may be the same or n represent a hydrogen atom or an alkyl group having 1 carbon atoms which may be substituted by a halog atom, a hydroxyl group or a cyano group, or togeth form a pyrrolidine, piperidine, or morpholine ring wi the nitrogen to which they are attached, and X is halogen atom.

2. A method according to claim 1, wherein $R^1$ and together form a piperidine ring or a morpholine ri with the nitrogen to which they are attached.

3. A method according to claim 1, wherein vi diseases in said plants are selected from the group cc sisting of tobacco mosaic virus, cucumber mosaic vir cucumber green mottle mosaic virus, potato X vir lettuce mosaic virus and melon necrotic spot virus.

4. A method according to claim 3, wherein t viruses are selected from the group consisting of bacco mosaic virus, cucumber mosaic virus and cucu ber green mottle mosaic virus.

5. A method according to claim 1, wherein $R^1$ and which may be the same or not, represent a hydrog atom, a linear alkyl group having 1-3 carbon atoms β-hydroxyethyl group, a β-cyanoethyl group or a hydroxy-γ-halopropyl group.

6. A method according to claim 1, wherein the po mer is a copolymer produced from two compour selected from the following groups (A) and (B);

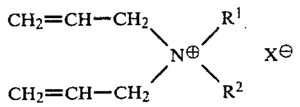

wherein, $R^1$ and $R^2$ represent an alkyl group having carbon atoms and X represents a halogen atom.

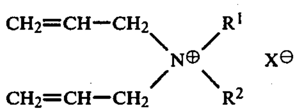

(B)

erein, $R^1$ represents a hydrogen atom, $R^2$ represents ꞵ-hydroxyethyl group, a $\beta$-cyanoethyl group or a ıydroxy-$\gamma$-chloropropyl group, and X represents a ogen atom.

'. A method according to claim 1, wherein the poly- r is a homopolymer of a compound expressed by the lowing general formula:

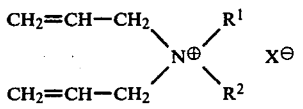

.erein $R^1$ and $R^2$ represent a hydrogen atom, a linear yl group having 1-3 carbon atoms, a $\beta$-hydroxyethyl ›up, a $\beta$-cyanoethyl group or a $\beta$-hydroxy-$\gamma$-chloro- ›pyl group and may form a pyrrolidine or together m a piperidine or a morpholine with the nitrogen :y attach to, and X represents a halogen atom.

ꞵ. A method according to claim 7, wherein $R^1$ and $R^2$ ›resent a methyl group, a ethyl group or a $\beta$- ꝺroxy-$\gamma$-chloropropyl group.

›. A method according to claims 6 or 7, wherein X ›resents a chlorine atom or a bromine atom.

10. A method according to claim 6, wherein the copolymer is produced from (3-chloro-2-hydroxy) propyl diallylamine hydrochloride and dimethyl allyl ammonium chloride.

11. A method according to claim 6, wherein the rotational viscosity of the copolymer is in the range of from 1.5 to 30 cps in 0.2 wt % aqueous solution at 20° C.

12. A method according to claim 7, wherein the rotational viscosity of the homopolymer is in the range of from 2.0 to 30 cps in 0.2 wt % aqueous solution at 20° C.

13. A method according to claim 1, wherein the plant is Solanaceae, Cucurbitaceae, Leguminosae, Crucifeceae or Rosaceae.

14. A method according to claim 1, wherein the plant is Solanaceae such as tobacco, tomato or green pepper, or Cucurbitaceae such as cucumber, watermelon or melon.

15. A method according to claim 14, wherein the plant is tomato or tobacco.

16. A method according to claim 1, wherein there is used a wettable powder for controlling viral diseases in plants comprising 70–99 parts by weight of the polymer of claim 1, and 1–30 parts by weight of a surface active agent.

17. A method according to claim 1 comprising applying to said plants an emulsion or solution for controlling viral diseases in plants comprising 10–60 parts by weight of the polymer of claim 1, 20–90 parts by weight of a solvent, and 1–20 parts by weight of a surface active agent.

* * * * *